(12) United States Patent
Ornatsky et al.

(10) Patent No.: US 8,236,511 B2
(45) Date of Patent: Aug. 7, 2012

(54) QUANTITATION OF CELLULAR DNA AND CELL NUMBERS USING ELEMENT LABELING

(75) Inventors: Olga Ornatsky, Richmond Hill (CA); Vladimir Baranov, Richmond Hill (CA)

(73) Assignee: DVS Sciences, Inc., Markham (CA)

( * ) Notice: Subject to any disclaimer, the term of this patent is extended or adjusted under 35 U.S.C. 154(b) by 0 days.

(21) Appl. No.: 13/333,301

(22) Filed: Dec. 21, 2011

(65) Prior Publication Data

US 2012/0164632 A1    Jun. 28, 2012

Related U.S. Application Data

(62) Division of application No. 11/674,440, filed on Feb. 13, 2007, now Pat. No. 8,101,368.

(60) Provisional application No. 60/772,589, filed on Feb. 13, 2006.

(51) Int. Cl.
*G01N 31/00* (2006.01)
*G01N 33/53* (2006.01)

(52) U.S. Cl. ........ 435/7.21; 435/7.1; 436/501; 436/518; 424/9.1; 424/520; 422/50; 530/300; 530/350

(58) Field of Classification Search ........................ None
See application file for complete search history.

(56) References Cited

U.S. PATENT DOCUMENTS 8,101,368 B2 *  1/2012  Ornatsky et al. ............. 435/7.21

* cited by examiner

*Primary Examiner* — Lisa Cook
(74) *Attorney, Agent, or Firm* — Senniger Powers LLP

(57) ABSTRACT

Methods and kits for the quantitation of cellular DNA and cell numbers are provided. Passive element uptake, element-labeled DNA intercalators, and element labeled affinity reagents are used to quantify DNA and cells. The DNA and the cells are analyzed by elemental analysis, including ICP-MS. The methods and kits provide a fast and accurate analysis of cellular DNA and cell numbers.

9 Claims, 11 Drawing Sheets

QUANTITATION OF CELLULAR DNA AND CELL NUMBERS USING ELEMENT LABELING

CROSS-REFERENCE TO RELATED APPLICATIONS

This application is a divisional of U.S. application Ser. No. 11/674,440, filed Feb. 13, 2007, which claims priority to U.S. Provisional Patent Application No. 60/772,589, filed Feb. 13, 2006, the contents of which are herein incorporated by reference.

COPYRIGHT AND LEGAL NOTICES

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

FIELD OF THE INVENTION

The present invention relates to a rapid and sensitive assay employing elemental analysis for cell enumeration and cell proliferation using element-labeled intercalators together with element-tagged affinity reagents to determine the cell type in a mixed cell population.

INTRODUCTION

"Intercalation" is functional non-covalent insertion of a ligand between two molecular moieties. For example, the molecular moieties can be nucleotide base units of double-stranded nucleic acid[1] or amino acids in proteins, to name a few. DNA intercalating reagents are extensively used as sensitive molecular probes and therapeutic agents owing to their site selective targeting and reactivity[2;3]. Metallointercalators are intercalating reagents having a transition-metal complex core. Metallointercalators can be bound by non-intercalating and intercalating ligands. For example, metallointercalators can be bound by two non-intercalating ligands and one intercalating ligand. The intercalator can comprise other elements (i.e., non-metal elements, such as propidum iodide with two iodide molecules) for DNA quantitation. "Elemental analysis" is a process where a sample is analyzed for its elemental composition and sometimes isotopic composition. Elemental analysis can be accomplished by a number of methods, including, but not limited to: I. optical atomic spectroscopy, such as flame atomic absorption, graphite furnace atomic absorption, and inductively coupled plasma atomic emission, which probe the outer electronic structure of atoms; II. mass spectrometric atomic spectroscopy, such as inductively coupled plasma mass spectrometry, which probes the mass of atoms; III. X-ray fluorescence, particle induced x-ray emission, x-ray photoelectron spectroscopy, and Auger electron spectroscopy which probes the inner electronic structure of atoms.

"Elemental analyzer" is an instrument functionally designed for the quantitation of atomic composition of a sample employing one of the methods of elemental analysis.

"Particle elemental analysis" is a process where an analyzed sample, composed of particles dispersed in a liquid (beads in buffer, for example), is interrogated in such a manner that the atomic composition is recorded for individual particles (bead-by-bead, for example). An example of the analytical instrument is a mass spectrometer-based flow cytometer.

"Solution elemental analysis" is a process where an analyzed sample is interrogated in such manner that the atomic composition is averaged over the entire solution of the sample.

"Element tag" or "tag" is a chemical moiety which includes an elemental atom or multitude of elemental atoms which one or many isotopes attached to a supporting molecular structure. In one instance an element tag may comprise a metal-chelate polymer with an attachment group. The attachment group may include, but is not limited to, pyrrole-2,5-dione (maleimido), sulfonic acid anion, or p-(chloromethyl) styrene (for thiol, N-terminus, or C-terminus, respectively). Other means are known to those skilled in the art.

The term "antibody" includes monoclonal antibodies, polyclonal antibodies, multispecific antibodies (e.g. dual specificity antibodies), and antibody fragments, both natural and recombinant, as long as they exhibit the desired biological activity or something functionally similar.

An "antigen specific antibody labeled with an element tag" comprises and antibody which has been subsequently reacted with an element tag which allows the antigen-antibody complex to be detected and quantified by solution elemental analysis.

An "affinity product" or "affinity reagent" refers to biological molecules (antibody, aptamer, lectin, sequence-specific binding peptide, etc.) which are known to form highly specific non-covalent bonds with respective target molecules (peptides, antigens, small molecules, etc.). Affinity reagent labeled with a unique element tag is an affinity product labeled with an element tag that is unique and distinguishable from a multitude of other element tags in the same sample.

A "transition element" means any element having the following atomic numbers, 21-29, 39-47, 57-79, and 89. Transition elements include the rare earth elements, lanthanides, and noble metals (Cotton and Wilkinson, 1972).

An "internal standard" is defined as a known amount of a compound, different from analyte, that is added to the unknown. Signal from analyte is compared with signal from the internal standard to find out how much analyte is present. An internal standard normally is used when performing mass spectrometry quantitation. An internal standard can also be used by other means known to those skilled in the art.

Fixing and permeabilization refers to chemical cross-linking of cellular components by agents known to those skilled in the art, and may include but not limited to glutaraldehyde, formaldehyde, formalin, ethanol, methanol, etc., and creating holes in the cell membrane with detergents. Suitable detergents may be readily selected from among non-ionic detergents. These detergents may be used at a concentration between about 0.001% to about 0.1%. One currently preferred detergent is Triton X-100 (Sigma T9284). Examples of other suitable detergents include Igepal and Nonidet P-40. Other suitable detergents may be readily selected by one of skill in the art.

It is accepted in cell biology that the content of nucleic acids is a reasonable indicator of cell number owing to the tight regulation of DNA and RNA levels in the cells. DNA measurement is commonly used to estimate the number of cells in solid tumors as well as to characterize hematopoietic malignancies and monitor chemotherapy treatment[4;5]. Many studies demonstrate the prognostic significance of ploidy in human tumors. For example, trisomy 8 is one of the most frequent numerical chromosomal abnormalities observed in acute myelogenous leukemia (AML) and myelodysplastic syndrome (MDS)[6]. The content of DNA also reflects cell cycle progression. Cells grow through mitosis and the individual cells can be identified or classified, through their progression by mitosis, with a determination of the amount of DNA in the cell. In combination with antigen identification, the measurement of DNA indicates the ploidy or cell cycle phase for a subset of cells defined by the antigen in heterogeneous cell populations, or the distribution of a particular antigen through the cell cycle[7;8].

Reagents that measure cell proliferation and cell numbers are important diagnostic and research tools. Standard methods of cell enumeration include BrdU (5-bromo-2'-deoxyuridine); 3H-thymidine incorporation into replicating cells during proliferation, and the measurement of total nucleic acid content of lysed cells with a colorimetric (diphenylamine) reagent. Fluorescent DNA intercalating dyes in conjunction with flow cytometry have become the method of choice for rapid cell cycle and cell number measurements. Such DNA binding dyes as Hoechst 33258[9], propidium iodide[10], DAPI[11] and acridine orange[12] have been shown in many applications to accurately estimate cell numbers. However, these reagents suffer from relatively low fluorescence enhancements upon binding nucleic acids, low extinction coefficients and have high intrinsic background fluorescence. Recently a novel class of cyanine dyes and a sensitive nucleic acid stain-based assay have been developed by Molecular Probes Inc. which obviates these problems[13].

Metallointercalators interact with double-stranded DNA through electrostatic forces—groove binding and intercalation, for example. Substantial research has been devoted to the photoluminescent[14-16] and photo-oxidizing properties of metallointercalators[17-21]. 9,10-Phenanthrenequinone diimine (phi) complexes of rhodium(III) (Rh(III)) have been shown to bind tightly (Kd<$10^{-8}$M) to double stranded DNA by intercalation in the major groove[22-24] and undergo a variety of photoinduced reactions with DNA[20;25-27]. From photo-footprinting experiments Barton et al. (1992) concluded that Rh(phi)$_2$(bpy)$^{3+}$ has a rigid rhodium complex that can occupy directly all sites not obstructed by DNA binding proteins, and at rhodium/base pair rations of 2:1 binding to DNA is sequence neutral and random[28;29]. Recent work from the same group has also shown that metallointercalators which targeted major groove sites bind poorly to double-stranded RNA[30;31]. However, other experiments indicate that the apposition of several non-canonical bases as well as stem-loop junctions and bulges in tRNA could result in intimately stacked structures with opened major grooves accessible for metallointercalator binding[31].

Recently, Inductively Coupled Plasma Mass Spectrometry (ICP-MS) has been introduced to the field of protein and cell surface antigen identification via ICP-MS-linked immunoassays using metal containing immunoreagents such as gold and lanthanide-conjugated antibodies[32-35]. ICP-MS as a analytical detector offers absolute quantification that is largely independent of the analyte molecular form or sample matrix. Secondly the abundance sensitivity of ICP-MS, a measure of the overlap of signals of neighboring isotopes, is large (>$10^6$ for the quadrupole analyzer), and this ensures independence of the detection channels over a wide dynamic range. The third key property is that ICP-MS is very sensitive; it was demonstrated that ICP-MS-linked immunoassays can be at least as sensitive as radioimmunoassay.

ICP-MS is extensively used to study natural and induced metal incorporation into bacteria[36-39], plants[40] and as a tool in metalloproteomics research[41].

The choice of the element to be employed in the methods of the present invention is preferably selected on the basis of its natural abundance in the sample under investigation and whether the element is cytotoxic to the sample under investigation.

Most metals of the transition and rare earth groups are anticipated for use in passive uptake labeling of cultured cells. It is wise to choose elements that have low or no cytotoxicity and have a low abundance in growth media and biological samples. For example, vanadium and mercury can be toxic to certain cells, while Fe, Cu and Zn can be present in high concentrations in some cell culture media. On the other hand, Pr, Ho, Tb, La, for example are normally well tolerated by mammalian cells and are not abundant in the environment.

Metallointercalators are synthesized using aromatic compounds as ligands for DNA binding and transition-metal complex cores. Metallointercalators can incorporate many types of metal centers such as Ru, Rh, Os, Co, Re, and Ir. A vase number of ligands are known to those skilled in the art (bipyridine, 9,10-phenanthrene quinone diimine, 1,10-phenanthroline, etc.). Other element labeled DNA intercalators can also be used.

An unusual isotope composition of the tag element can be used in order to distinguish between naturally present elements in the sample and the tag material. It is advantageous if the relative abundance of the tag elements is sufficiently different from the relative abundance of elements in a given sample under analysis. By "sufficiently different" it is meant that under the methods of the present invention it is possible to detect the target elemental tag over the background elements contained in a sample under analysis. Indeed, it is the difference in the inter-elemental ratios of the tagging elements and the sample matrix that can be used advantageously to analyze the sample.

It is feasible to select elemental tags, which do not produce interfering signals during analysis (i.e., do not have overlapping signals due to having the same mass). Therefore two or more analytical determinations can be performed simultaneously in one sample. Moreover, because the elemental tag can be made containing many copies of the same atoms, the measured signal can be greatly amplified.

SUMMARY OF THE INVENTION

These and other features of the applicant's teachings are set forth herein.

An aspect of the applicant's teachings is to provide a method to quantify the number of cells in a sample comprising cells, the method comprising: culturing the sample with an element to passively accumulate the element in the cells in the sample; washing the cells to remove non-accumulated element; measuring the element in a known quantity of the cells by elemental analysis to determine the amount of accumulated element per cell; measuring the element in the sample by elemental analysis; and quantifying the number of cells in the sample.

Another aspect of the applicant's teachings is to provide a method to quantify antigen content per cell in a cell sample wherein the cells of the sample comprise an antigen, comprising: culturing the cells of the sample in the presence of a first element wherein the cells passively accumulate the first element; calculating the number of cells in the sample; removing non-accumulated first element; incubating the cells with antigen specific affinity products labeled with a second element tag; removing unbound affinity products; simultaneously measuring the passively accumulated first element and the amount of the bound affinity product labeled with a second element tag by elemental analysis; and calculating the antigen content per cell.

Another aspect detection and measurement of a first element in a sample, where the measured first element originated from the first element passively accumulated by cells, comprising: (a) a soluble compound of a first element for addition to a cell media. The kit can further comprise instructions for (i) spiking a cell media with the soluble compound of the first element, (ii) separating bound first element from unbound first element, and (iii) detecting and measuring the passively accumulated first element by elemental analysis. The kit can further comprise (a) a second element for directly tagging an analyte specific affinity product; and (b) an analyte specific affinity product. The kit can further comprise instructions for (i) directly tagging the analyte specific affinity product with the second element; (ii) combining the tagged analyte specific affinity product with at least one type of an analyte and analyte complex under conditions in which the tagged analyte specific affinity product binds with at least one of intra- or/and extra-cellular analyte and analyte complex, (iii) separating bound affinity product from unbound affinity product, and (iv) detecting and measuring the second element by elemental analysis. The kit can further comprise an analyte specific affinity product, wherein the analyte specific affinity product is directly tagged with a second element.

Another aspect of the applicant's teachings is to provide a kit for the detection and measurement of a first element in a sample, where the measured first element originated from a DNA intercalator, comprising: (a) a DNA intercalator comprising a first element. The kit can further comprising instructions for (i) incorporating the first element containing intercalator into the DNA within the cells of the sample, (ii) separating bound intercalator from unbound intercalator, and (iii) detecting and measuring the inter-calator comprising the first element by elemental analysis. The kit can further comprise (a) a second element for directly tagging an analyte specific affinity product; and (b) an analyte specific affinity product. The kit can further comprise instructions for (i) directly tagging an analyte specific affinity product; (ii) combining the tagged analyte specific affinity product with at least one type of an analyte and analyte complex under conditions in which the tagged analyte specific affinity product binds with at least one of intra- or/and extra-cellular analyte and analyte complex, (iii) separating bound affinity product from unbound affinity product, and iv) detecting and measuring the second element by elemental analysis. The kit can further comprise an analyte specific affinity product wherein the analyte specific affinity product is directly tagged with a second element.

BRIEF DESCRIPTION OF THE DRAWINGS

FIG. 5. Detection of the internal Rh(III) labels (A) and the surface Au labels (B) by particle elemental analysis with ICP-MS operated in transient mode. Single cell analysis of surface antigen CD34 expression (Au) and intracellular DNA (Rh) content were analyzed. KG-1a cells were treated with intercalator and reacted with anti-CD34 antibodies followed by Au-labeled secondary antibodies.

Corresponding reference characters indicate corresponding parts throughout the drawings.

DESCRIPTION OF THE VARIOUS EMBODIMENTS

Aspects of the applicant's teachings may be further understood in light of the following examples, which should not be construed as limiting the scope of the present teachings in any way.

Experiment 1.

Figure 7:
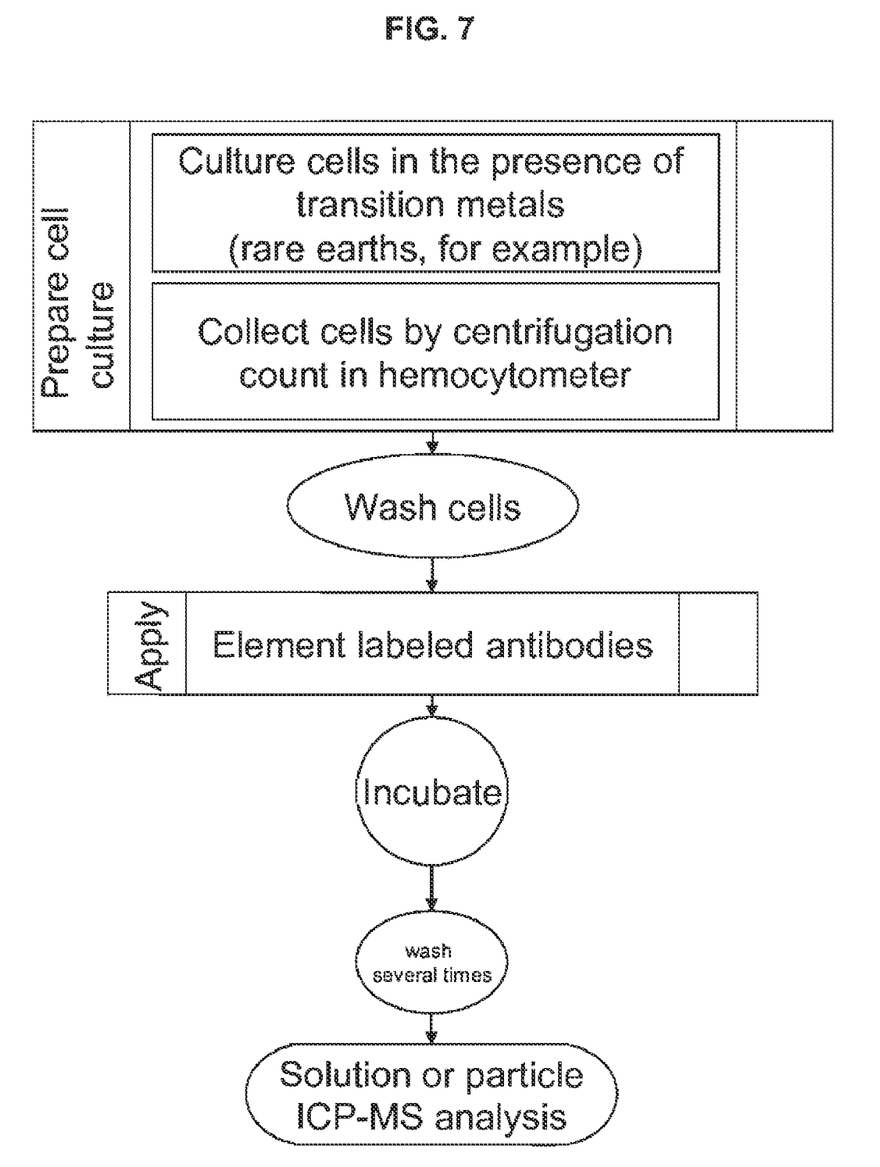
FIG. 7. Chart showing a method to quantify antigen content per cell, in accordance with the invention.

One embodiment can be demonstrated by example of rhodium (Rh) and palladium (Pd) in mixed cell populations with surface marker identified by europium (Eu). The experiment was set up to investigate if metals passively accumulated by cells could be indicative of cell number and cell type. A work flow chart is presented in FIG. 7. For this purpose two different leukemia cell lines were cultured for 72 hours in growth media supplemented with very low amounts of rare earth metals: 100 ppb Rh was added to MBA-1 cells, and 500 ppb Pd was added to KG-1a cells which express the cell surface marker. During the three days of cell culture, aliquots of cells were tested for viability with trypan blue. No excessive cell death was recorded due to the presence of metals in media. Cells were collected by centrifugation (1200 rpm, 10 minutes), washed once in PBS/10% FBS and counted in a hemocytometer. Serial dilutions were prepared to give $1 \times 10^6$, $0.5 \times 10^6$, $1 \times 10^5$, $1 \times 10^4$, $1 \times 10^3$, and $1 \times 10^2$ KG-1a cells in a population of MBA-1 cells ($1 \times 10^6$) per tube in triplicates (Table 1). In this example Pd will reflect the number of KG-1a cells and the presence of surface marker CD34 will specify the cell type, while MBA-1 cells are marked by Rh. Immunolabeling was carried out by adding anti-CD34 antibodies to tubes containing decreasing amounts of live KG-1a cells and incubating for 45 minutes on ice. Negative control tubes were reacted with the IgG1 isotype control immunoglobulins.

Figure 1A:
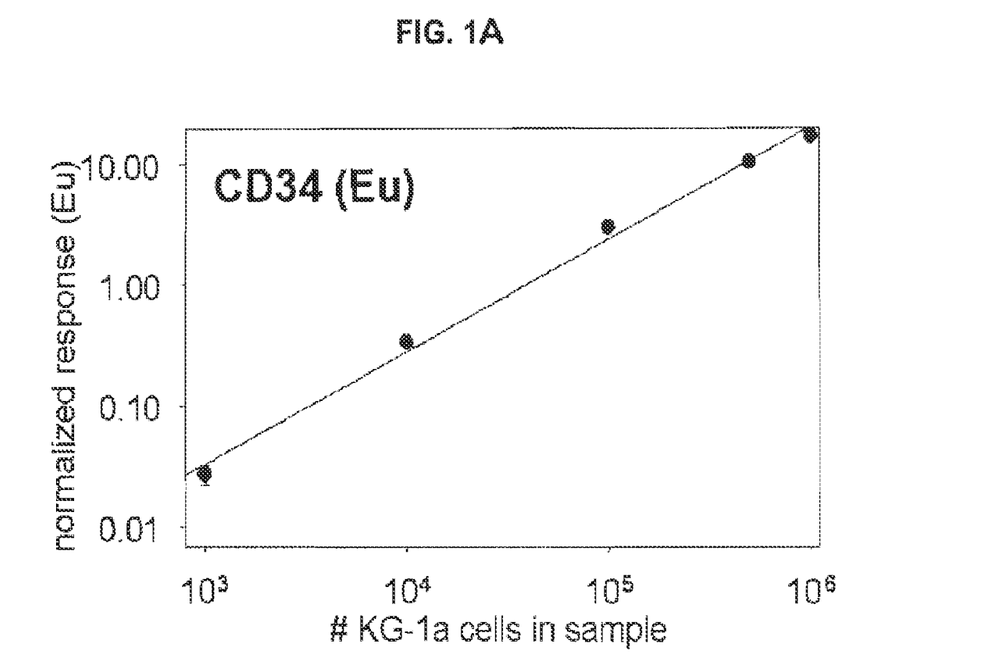
FIG. 1A. Upper plot—linear response between number of KG-1a cells present in each sample and amount of CD34 antigen detected as signal from Eu normalized to Ir internal standard (Eu/Ir) with background subtracted. Lower plot—relationship of KG-1a cell numbers and accumulated metal, palladium, normalized to Ir internal standard (Pd/Ir).
Figure 1B:
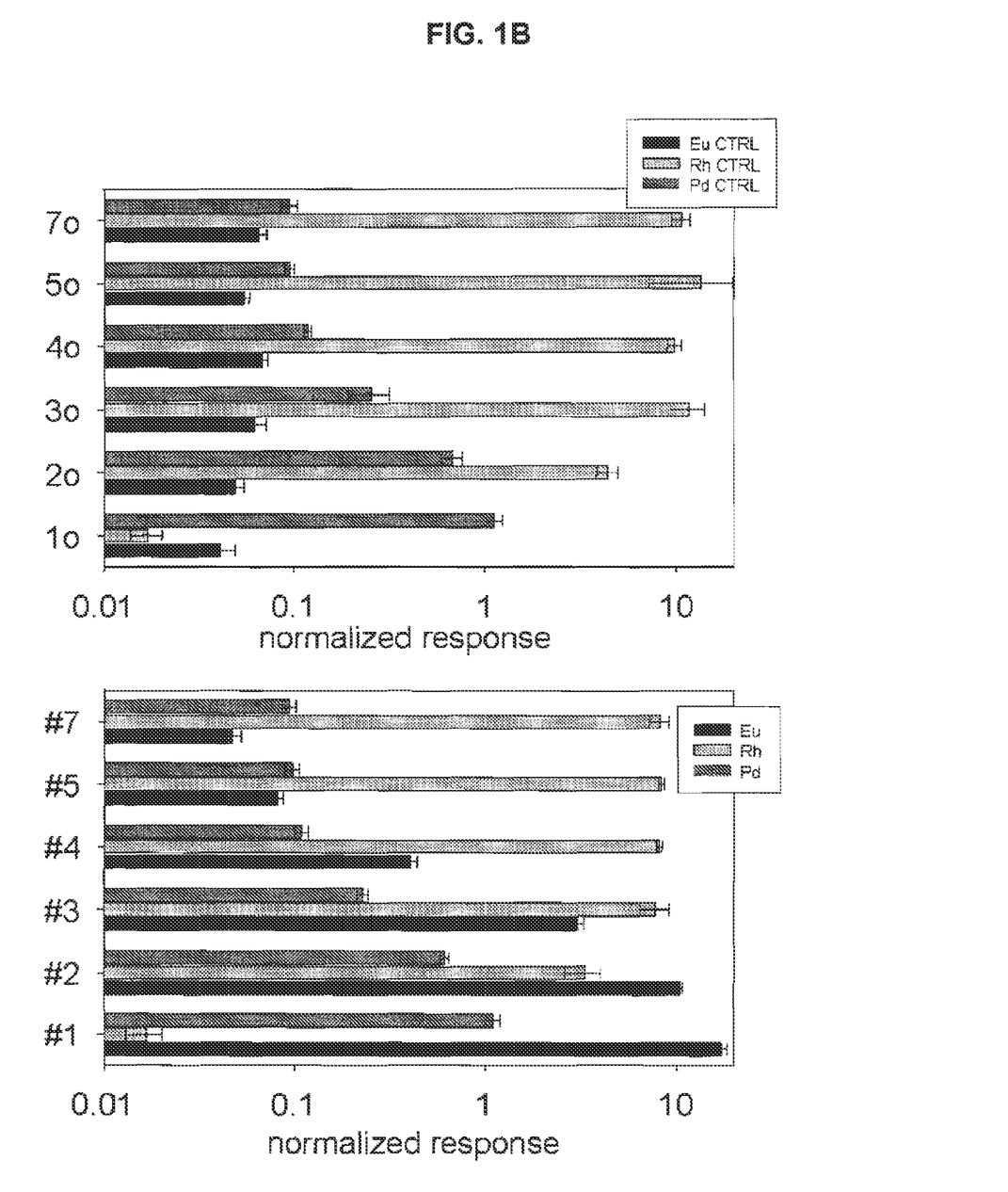
FIG. 1B. Upper bar graph—mixed cell samples (1o,2o,3o, 4o,5o,7o on the Y-axis) were incubated with negative control isotype specific immunoglobulin and Eu-labeled secondary antibodies; analyzed for Eu, Pd, and Rh; signal values are relative to Ir internal standard. Lower bar graph—samples (#1, #2, #3, #4, #5, #7 on the Y -axis) were incubated with anti-CD34 primary and Eu-labeled secondary antibodies; analyzed for Eu, Pd, and Rh; signal values are relative to Ir internal standard.

After three low speed centrifugation washes with PBS/10% FBS all samples were incubated with biotinylated anti-mouse antibodies. This was followed by several washes, and Eu-labeled streptavidin (DELFIA, Perkin Elmer) was added to all samples as the last step in the immunolabeling procedure. Unreacted Eu-strepavidin was eliminated by three final washes. Cell pellets were then dissolved overnight in 75 ul of concentrated HCL. Prior to ICP-MS analysis, an equal volume of 1 ppb iridium standard (Ir) was added to each sample. Three independent experiments were performed. ICP-MS acquisition of Eu, Rh and Pd signals are presented in FIG. 1A and FIG. 1B. In this example, the detection limit for an abundant biomarker (CD34) is ~1000 cells in the presence of $1 \times 10^6$ unrelated cells. Therefore, passive metal accumulation by cells can be used for normalization of a biomarker concentration in solution and particle elemental analysis.

TABLE I

Samples containing mixed populations of cells cultured in media supplemented with palladium (Pd) or rhodium (Rh).

| Sample (Rh) | KG1-a (Pd) | MBA-1 |
|---|---|---|
| #1, 1o | 1e6 | 0 |
| #2, 2o | 5e5 | 5e5 |
| #3, 3o | 1e5 | 1e6 |
| #4, 4o | 1e4 | 1e6 |
| #5, 5o | 1e3 | 1e6 |
| #7, 7o | 0 | 1e6 |

Although antibodies were used in the above example, it is to be understood that any affinity product can be used in place of the antibody as is known to those skilled in the art. Further it is possible to analyze more than one analyte/antigen by using more than one antibody or affinity product.

Although the analyte/antigen was found on the surface of the cell in the above example, it is to be understood that analytes/antigens can also be found within the cell and methods for the analysis of these internal analytes/antigens are included in this invention.

Experiment 2

Figure 2:
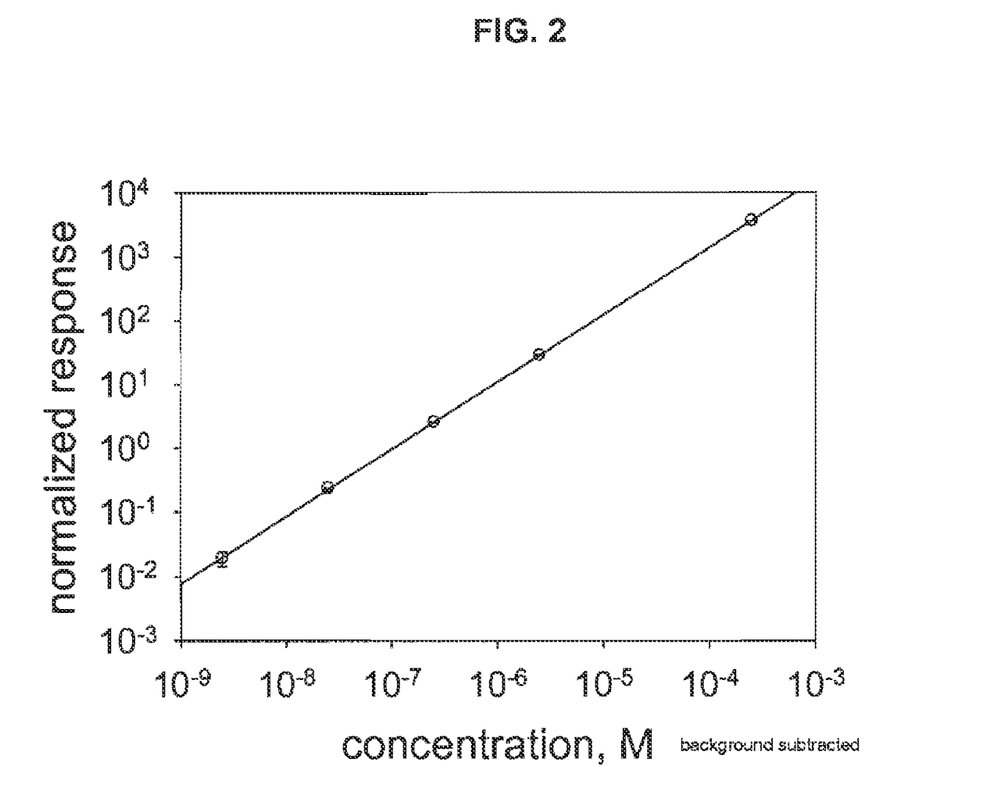
FIG. 2. Linear concentration dependence between amounts of Rh(III) metalointercalator and signal obtained from treated cells (normalized response).

Yet another embodiment can be demonstrated by example of rhodium-containing (Rh(III)) metallointercalator binding to cells. Binding of an intercalator to DNA is governed by the law of mass action. Assuming that a mammalian cell in G1 phase has $3.3 \times 10^9$ DNA base pairs of which only 10-70% are free from protein interaction (nucleosomes) and available for binding with the intercalator (one molecule per two base pairs at saturation), the number of molecules of dye needed is approximately $1-10 \times 10^8$. Thus for $[Rh(phi)_2 bpy]Cl_3$, with 671 MW, 1 ml of 200 uM solution should be 100-fold excess of intercalator over DNA binding sites for $1 \times 10^6$ cells. The binding of various amounts of the Rh(III) intercalator with cultured cells was assessed. MBA-1 cells were fixed in 3.7% formaldehyde/PBS for 15 minutes, followed by permeabilization with 0.3% TritonX-100/PBS; washed once with PBS and incubated for 45 minutes with 1 ml of increasing concentrations of $[Rh(phi)_2 bpy]Cl_3$ from 2.5 nanoM to 250 microM. Each sample contained $3 \times 10^6$ cells, run in triplicates. Following washing, the cell pellets were treated with concentrated HCl, mixed with an equal volume of 1 ppb Ir internal standard, and analyzed in solution by ICP-MS. FIG. 2 shows a linear normalized signal response. Therefore, it is observed that the intercalator can bind to DNA in a very broad range of concentrations without reaching a saturation limit.

Figure 3:
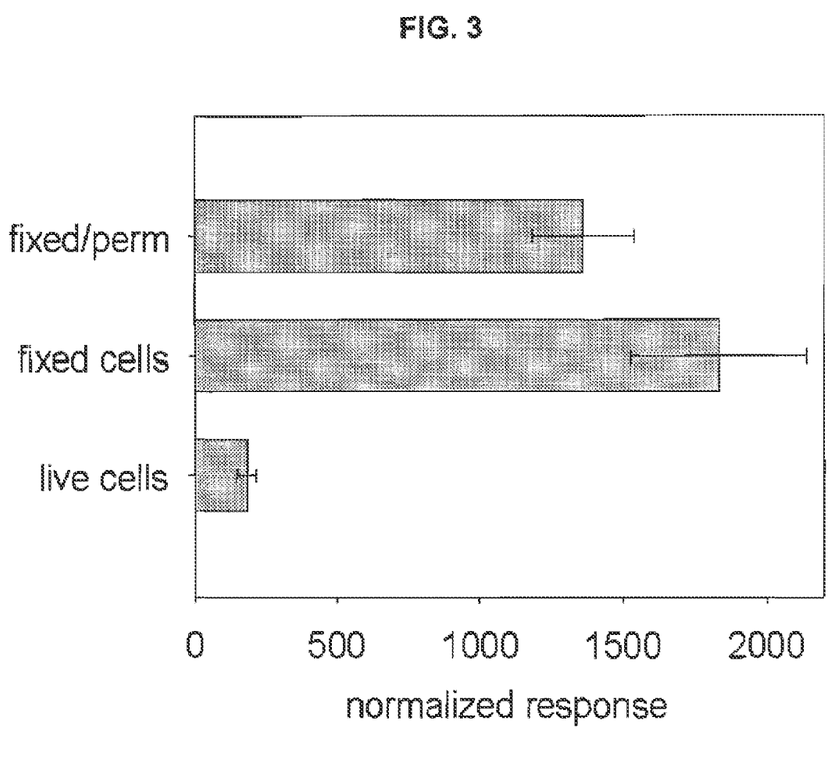
FIG. 3. Normalized response for Rh obtained after treating live, or fixed, or fixed/permeabilized (fix/perm) MBA-1 cells with Rh(III) complex.

Reactivity of the Rh(III) metallointercalator with fixed and fixed/permeabilized versus live cells was also examined. Equal amounts of MBA-1 cells ($1 \times 10^6$) were either fixed/permeabilized as above, fixed in 3.7% formaldehyde alone or left untreated (live cells). After two washes in PBS the cells were incubated with 200 uM $[Rh(phi)_2 bpy]Cl_3$ for 30 minutes; washed three more times and dissolved in HCl. FIG. 3 shows a representative graph of two experiments. As evident from FIG. 3, in live cells the Rh(III) complex is membrane impermeable, while fixation and fixation/permeabilization permit DNA and metal complex intercalation to similar levels. Therefore, it is observed that non-specific binding of the intercalator to the cell surface is very limited; the complex is not internalized by live cells and the concentration of the Rh(III) complex corresponds to DNA content. Exact ratio of the intercalator to DNA content was investigated in following experiments.

Experiment 3.

Figure 4:
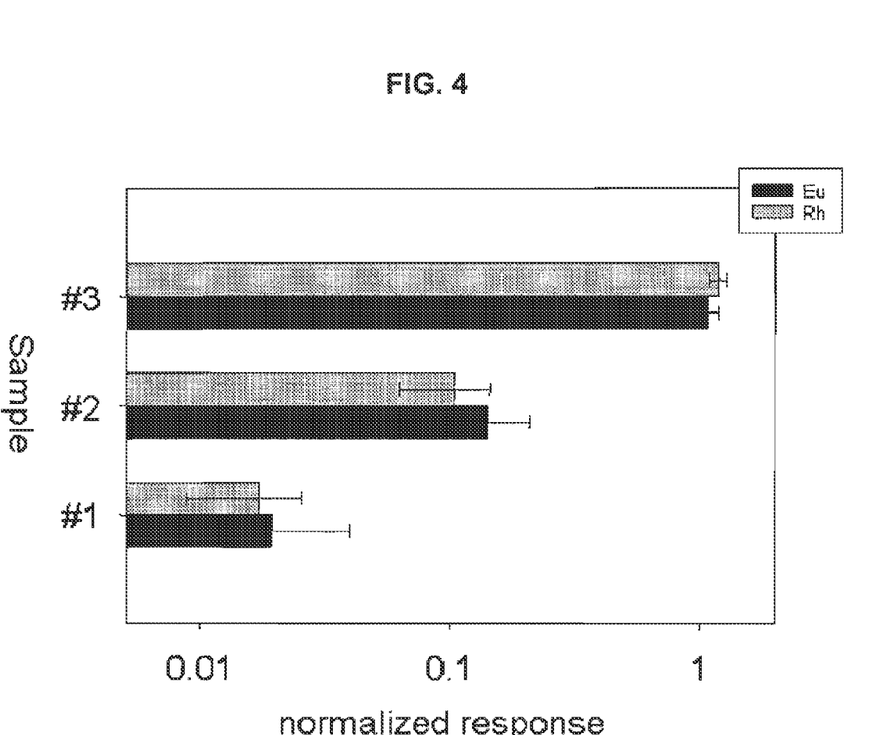
FIG. 4. Simultaneous identification of cellular DNA (Rh) and surface antigen CD33 (Eu) by solution elemental analysis. MBA-1 cells were treated with Rh(III) complex and reacted with anti-CD33 antibodies followed by Eu-labeled secondary antibodies. Sample #1 contains $3 \times 10^4$, sample #2—$3 \times 10^5$, and sample #3—$3 \times 10^6$ cells.
Figure 9:
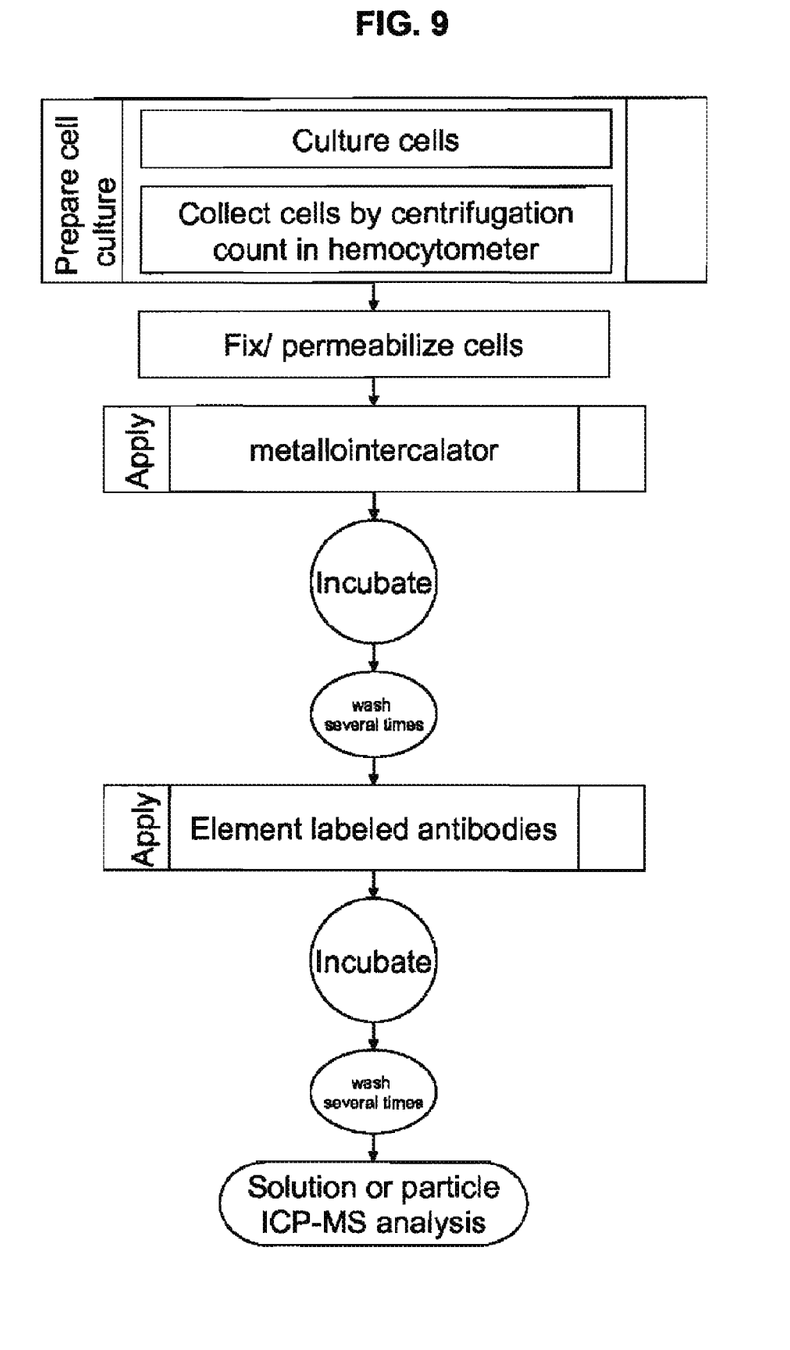
FIG. 9. Chart showing a method to determine DNA and antigen content per cell, in accordance with the invention.

Yet another embodiment can be demonstrated by example of DNA labeling with Rh(III) metallointercalator and antigen CD33 surface labeling using solution and particle elemental analysis as shown in FIG. 4 and FIG. 9.

MBA-1 cells were fixed/permeabilized with 3.7% formaldehyde and 0.3% Triton X-100 and labeled with Rh(III) intercalator (250 microM). Triplicate samples with $3 \times 10^4$, $3 \times 10^5$, and $3 \times 10^6$ cells per tube were prepared. Cells were then incubated with the primary anti-CD33 antibody, followed by secondary Eu-labeled anti-mouse antibody. Cells were washed in 0.65 μm centrifugal spin filters (Durapore). After the final wash, filter units were placed over new eppendorf tubes and 80 microL of concentrated HCl were added. Overnight digestion of cellular material was followed by centrifugation and the filtrate was collected, combined with equal volume of Ir internal standard and subjected to ICP-MS. FIG. 4 shows simultaneous identification of Rh (representing cell numbers) and Eu (representing cell surface antigen CD33) by solution elemental analysis.

Experiment 4

Figure 5A:
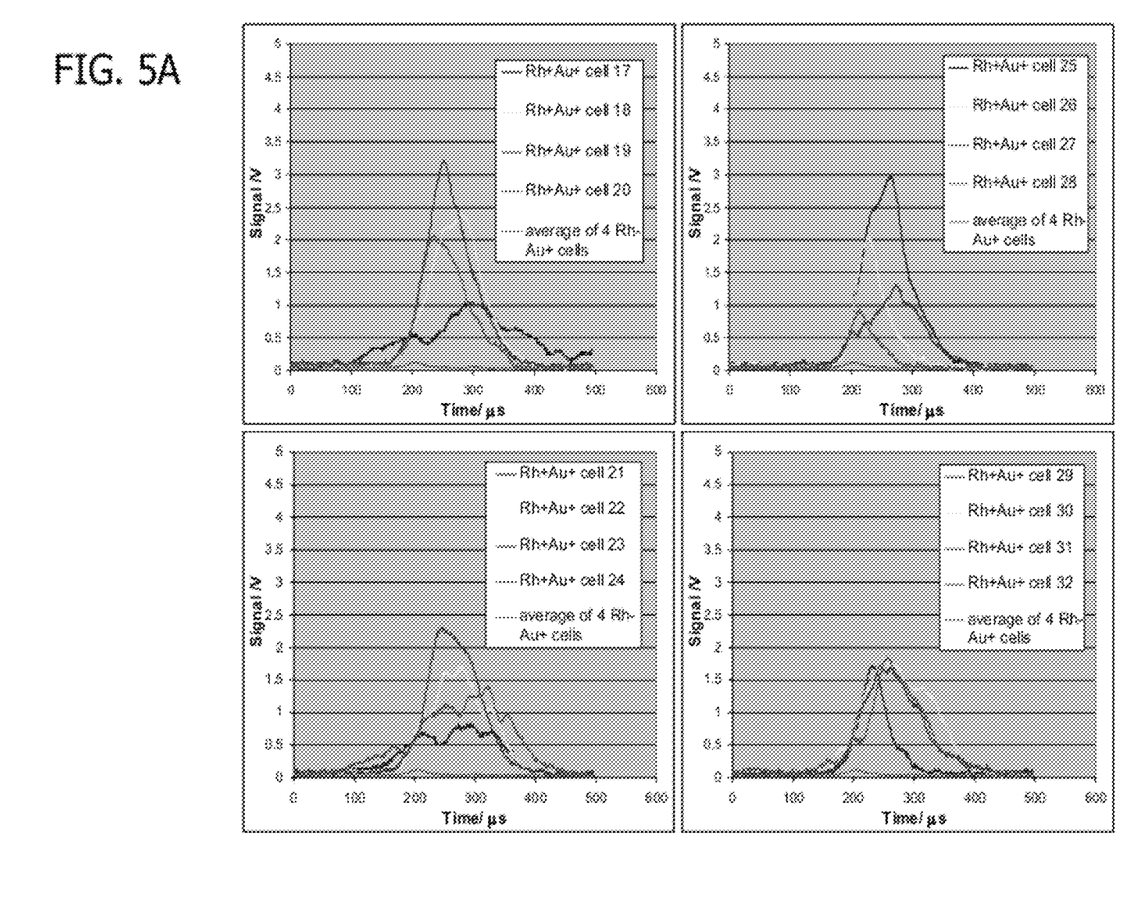
Figure 5B:
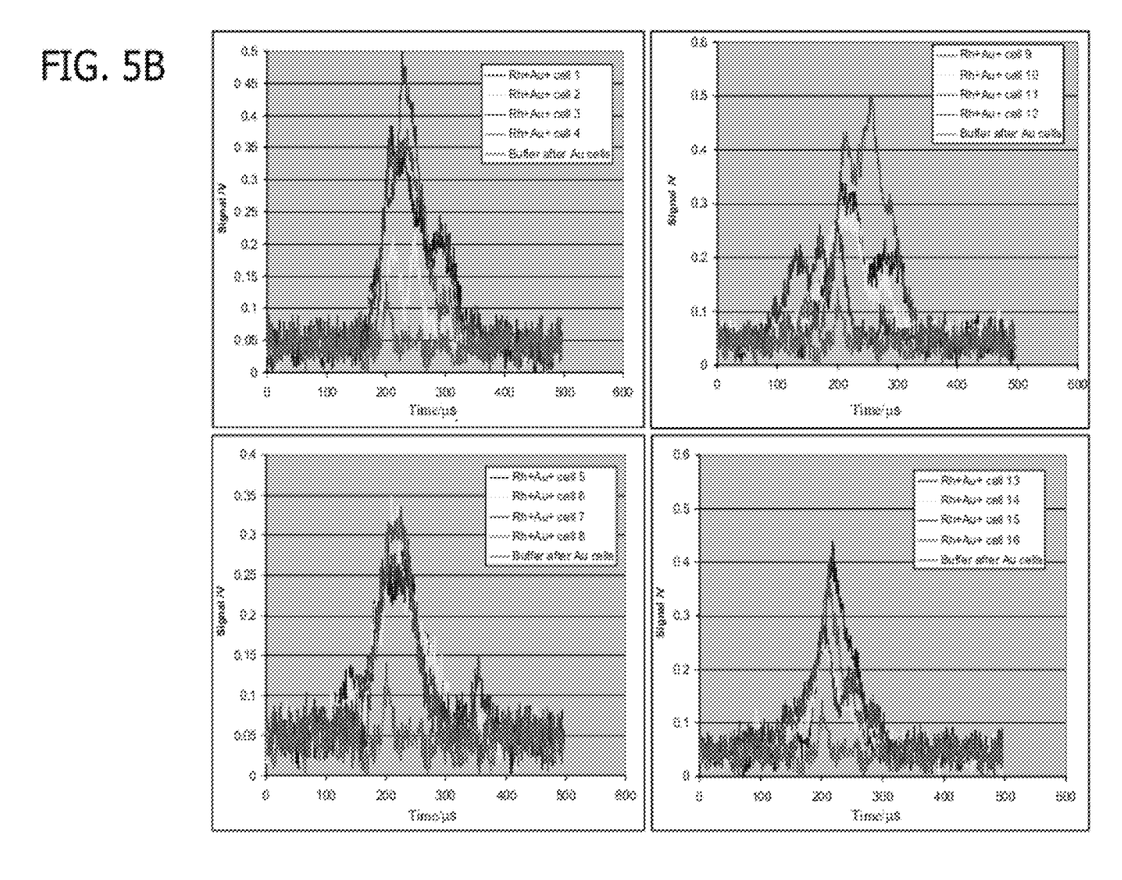

In another embodiment, DNA bound to Rh(III) intercalator and surface antigen expression were detected in single cells by particle elemental analysis with ICP-MS operated in transient mode (for flow chart see FIG. 9). For these experiments, KG-1a cells were treated with the Rh(III) intercalator as described above. The CD34 surface antigen was detected via primary anti-CD34 antibody and secondary gold (Au) labeled anti-mouse antibody. A cell suspension of $1 \times 10^5$ cells/ml was prepared in 50 mM ammonium bicarbonate buffer, pH7.4. The suspension was aspirated into the ion source of Elan6100 ICP-MS at a rate of 40 microliters per minute, resulting in an average rate of 67 cells per second. Two sets of experiments were conducted: one with the mass analyzer set to m/z=103 for $Rh^+$ detection, another—with m/z=197 for $Au^+$ detection. The detector was operated in the transient mode, e.g. the ion signals were detected from an output of the analog stage amplifier by storage oscilloscope (HP 54610B, Hewlett Packard), and the recorded signals were transferred to a computer for processing. FIG. 5 shows the examples of data collected for KG-1a cells, with analyzer set to m/z=103 (FIG. 5A) and to m/z=197 (FIG. 5B). In FIG. 5A, signals of Rh+ recorded for 16 Rh-positive Au-positive cells are compared to the averaged (n=4) signal for control Rh-negative Au-positive cells. Two kinds of transients were observed: more frequently appearing relatively short higher amplitude (70-110 microsecond full width at a half maximum) and less frequent long (>150 microsecond) with some fine structure and lower amplitude. The total number of ions recalculated from the areas of the peaks (after accounting for detector and amplifier gains) is similar between short and long transients, averaging at 500+−180 $Rh^+$ ions per transient. The number of ions in the transient should scale with the number of intracellular Rh(III)

labels, thus providing an evaluation of the cellular DNA and cell size. Experiments (not shown) with larger K562 cells (ca. 25 micrometer size compared to 10 micrometer for KG-1a) have shown that the transients contained on average 5600 $Rh^+$ ions. Detection of Au+ label from Rh-positive Au-positive KG-1a cells is shown in FIG. 5B. The signals are compared to the background of $Au^+$ signal measured after the sample introduction system was rinsed and washed-out for 20 minutes with 2% HCl (no $Au^+$ could be detected for the control Rh-positive Au-negative cells introduced before). The transient areas average at 72+−17 Au+ ions per peak.

Experiment 5.

Figure 6:
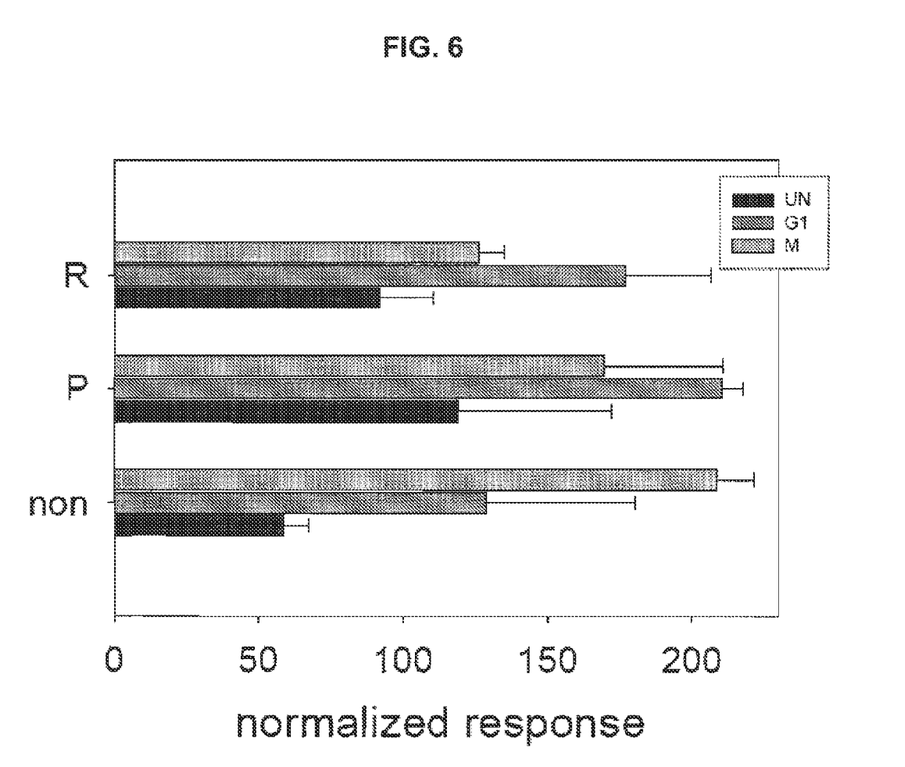
FIG. 6. DNA content (Rh, normalized response) depending on cell cycle phase. K562 cells were grown under normal conditions (UN) or treated for synchronization in the mitotic (M) or synthetic (G1/S) phase. Fixed cells were stained with Rh(III) complex and analyzed non-treated (non) or digested in Proteinase K (P) or RNAse A (R) solutions.
Figure 8:
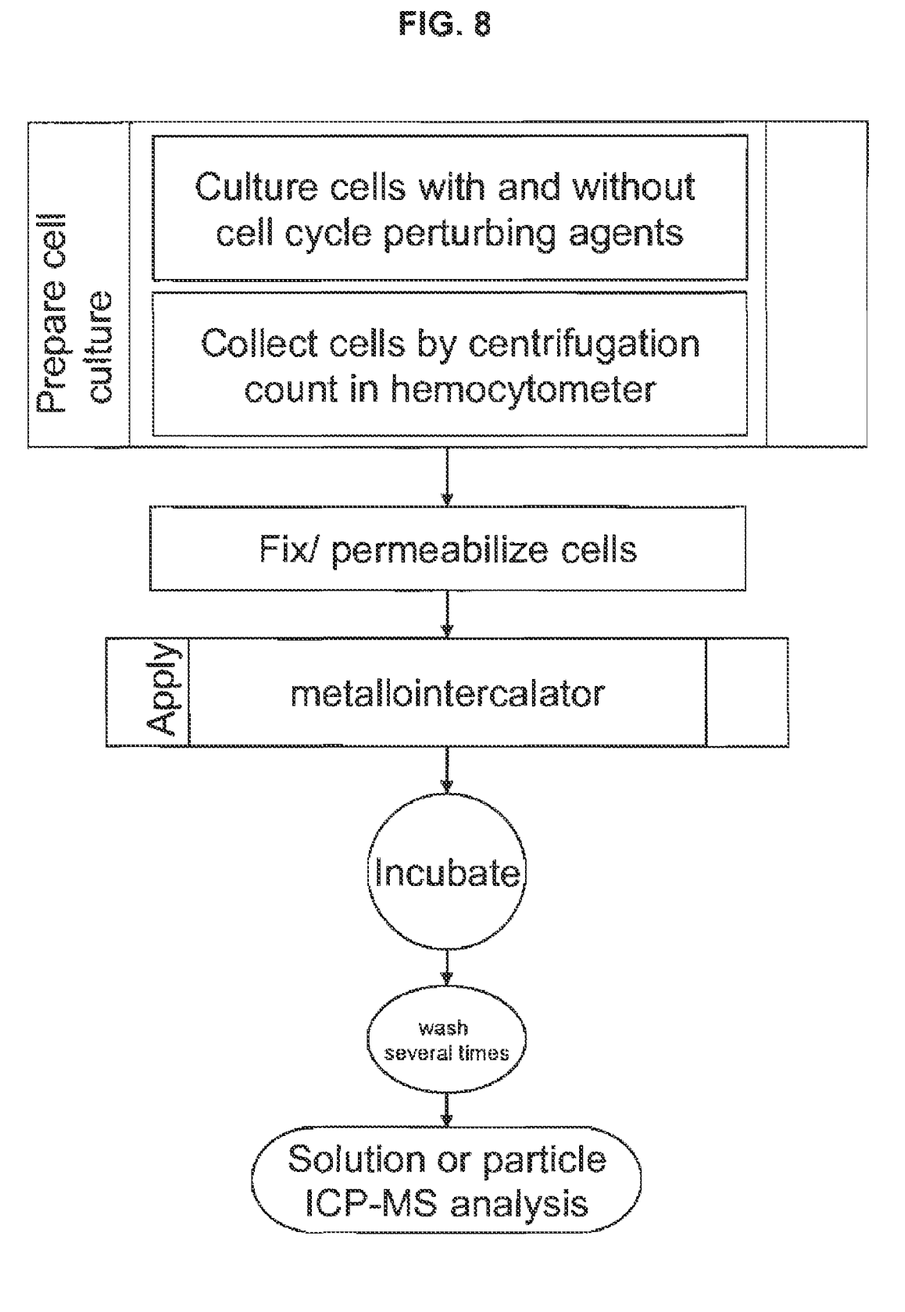
FIG. 8. Chart showing a method for determination of cell cycle phase, in accordance with the invention.

Yet another embodiment can be demonstrated by example of the DNA content in different cell cycle phases determined with metallointercalator (see flow chart of FIG. 8). Cells were synchronized in G1/S and G2/M phases of the cell cycle using a DNA synthesis inhibitor, thymidine, followed by a mitotic inhibitor, nocodazole. The DNA content of the G0/G1 phase is centered at 2n. Treatment with double thymidine results in a G1/S-phase arrested cell population with approximately 3n DNA content. Nocodazole addition following a single thymidine treatment arrests cells in the G2/M stage with 4n DNA content. K562 cells were treated with 2 mM thymidine added to culture medium for 17 hours. The cells were then washed and incubated in fresh media for 9 hours. At the end of this rest period the culture was split into two flasks—one received the second dose of 2 mM thymidine (double thymidine block) to arrest cells at G1/S; the other—0.2 ug/ml nocodazole (single thymidine-nocodazole block) to arrest cells at the M phase. The inhibitors were left in culture media for 17 hours. Finally, cells were collected, washed by centrifugation and prepared for DNA staining with propidium iodide (PI) or $[Rh(phi)_2 bpy]Cl_3$. Cells for PI staining were fixed in 75% ethanol at −20° C. for several hours and incubated with 10 microg/ml PI in 1.1% sodium citrate buffer with 1 mg/ml RNase according to standard protocol. Flow cytometry was done on FACSCalibur (BD Biosciences) and the results confirmed that after the double thymidine block the majority of cells were in G1/S, and after the M block practically all cells were in M phase. For Rh(III) complex staining the cells were fixed in 3.7% formaldehyde, washed and incubated in 100 uM $[Rh(phi)_2 bpy]Cl_3$ solution. After several washes the cells were digested in concentrated HCL and analyzed by ICP-MS. FIG. 6 illustrates content of DNA (normalized response) depending on the cell cycle phase: mitotic (M), synthetic (G1/S) or normal growth (UN). Moreover, the binding of intercalating metal compound was influenced by 10 U/ml Proteinase K (P) or 1 mg/ml RNAse A (R) digestion of stained cells. As evident from the graph, unsynchronized cells have considerably less DNA than mitotic cells, which have approximately two-fold higher amounts of nucleic acid than G1/S phase cells. Treatment of stained cells with enzymes shifts the detected Rh values due to enhanced binding of metallointercalator to naked DNA. As seen in FIG. 6, the amount of Rh is higher in enzyme treated samples R and P for cells in the G1/S phase and unsynchronized cultures (UN) compared to nontreated control cultures (non). This may be the result of protease degradation of DNA binding proteins and hence more nucleic acid being exposed to binding with the metallointercalator for P samples. In the case of RNAse A treatment—degradation of small RNA molecules bound to DNA such as siRNA that may block interaction of intercalator and DNA may lead to higher detected Rh values. On the other hand, during mitosis, when DNA is tightly packed into nucleosomes within the mitotic chromosomes enzymes fail to uncover "naked DNA" and this results in lower Rh signals.

Although ICP-MS was used in the above examples, it is to be understood that other forms of elemental analysis are encompassed in the applicant's teachings.

Kits.

Also provided are kits comprising the components for the analysis by elemental mass spectrometry for the methods described above.

For example, a kit is provided for the method of example 1 for the detection and measurement of elements, for example rare earth or transition elements in a sample, where the measured elements originated from an element passively accumulated by cells. The kit can comprise a soluble compound of the element for addition to a cell growth media. The kit may further comprise instructions for (i) spiking a cell growth media with the soluble compound of an element, (ii) separating bound material from unbound material, and (iii) detecting and measuring the passively accumulated element by elemental analysis.

A kit is also provided for the detection and measurement of an element, for example a rare earth or transition element, in a sample, where the measured elements originated from an element tag on an analyte specific affinity product that binds with at least one of intra- and/or extra-cellular analyte or analyte complex as described in example 1. The kit can comprise an element tag comprising the element for directly tagging an analyte specific antibody. The kit can further comprise instructions for (i) directly tagging an analyte specific affinity product; (ii) combining the tagged analyte specific affinity product with at least one type of an analyte and analyte complex under conditions in which the tagged analyte specific affinity product binds with at least one of intra- or/and extra-cellular analyte and analyte complex, (iii) separating bound material from unbound material, and (iv) detecting and measuring the element tag by elemental analysis.

Also provided is a kit comprising the combination of the components of the kits described above for the passive accumulation of elements by a cell and for an affinity product labeled with an element, wherein the affinity product is specific to an analyte in a cell or on the cell surface. The kit may further comprise an analyte specific affinity product, wherein the analyte specific affinity product is directly tagged with an element tag.

Also provided is a kit for the detection and measurement of an element, for example a rare earth or transition element in a sample, where the measured elements originated from a metal containing DNA intercalator for the method described in example 2. The kit can comprise a metal containing intercalator, and optionally instructions for (i) conditions appropriate to incorporate the element containing intercalator into the DNA within the cells of the sample, (ii) separating bound material from unbound material, and (iii) detecting and measuring the element containing intercalator by elemental analysis. Also provided is a combination kit comprising these components and the components for the kit for the method of detecting an analyte in or on a cell using a element labeled affinity product. Further, the kit can comprise an analyte specific affinity product, wherein the analyte specific affinity product is directly tagged with an element tag.

For any of the kits described above, the element can be measured using an ICP-mass spectrometer. The element can be an isotope or ion. The element can be selected from a group consisting of the transitions elements, noble metals, lanthanides, rare earth elements, gold, silver, platinum, rhodium, iridium and palladium. The affinity product can be selected from the group consisting of Fab', aptamer, antigen, hormone, growth factor, receptor, protein, SH2 peptides and nucleic acid. The element can include more than one atom of an isotope. The element can include a different number of atoms of each isotope.

Any of the kits can further comprise standards, a dilution buffer, an elution buffer, a wash buffer, and/or an assay buffer. Further, the kits can comprise two or more elemental tags for simultaneous determination of two or more analytes. The analyte can be a cytokine. A skilled worker, having read the specification, would understand how these components work in the methods of the present invention.

The kits described above can further comprise instructions for elemental mass analysis by mass spectrometry.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art All references cited in the disclosure are herein incorporated by reference.

REFERENCE LIST

1. Long, E. C.; Barton, J. K. On Demonstrating Dna Intercalation *Accounts of Chemical Research* 1990, 23, 271-73.
2. Barton, J. K. Targeting Dna Sites with Chiral Metal-Complexes *Pure and Applied Chemistry* 1989, 61, 563-64.
3. Chow, C. S.; Barton, J. K. Transition-Metal Complexes As Probes of Nucleic-Acids *Methods in Enzymology* 1992, 212, 219-42.
4. Labarca, C.; Paigen, K. A simple, rapid, and sensitive DNA assay procedure *Anal. Biochem.* 1980, 102, 344-52.
5. Plander, M.; Brockhoff, O,; Bariage, S.; Schwarz, S.; Rothe, O.; Knuechel, R. Optimization of three- and four-color multiparameter DNA analysis in lymphoma specimens *Cytometry Part A* 2003, 54A, 66-74.
6. Paulsson, K.; Fioretos, 1.; Strombeck, B,; Mauritzson, N.; Tanke, H. J.; Johansson, B. Trisomy 8 as the solo chromosomal aberration in myelocytic malignancies: a multicolor and locus-specific fluorescence in situ hybridization study *Cancer Genetics and Cyto genetics* 2003, 140, 66-69.
7. Gong, J.; Li, X.; Traganos, F.; Darzynkiewicz, Z. Expression of G(1) and 0(2) Cyclins Measured in Individual Cells by Multiparameter Flow-Cytometry A New Tool in the Analysis of the Cell-Cycle *Cell Proliferation* 1994, 27, 357-71.
8. Nowak, R.; Oelschlaegel, U.; Schuler, U.; Zengler, H.; Hofmann, R.; Ehfinger, O.; Andreeff, M. Sensitivity of combined DNA/immunophenotype flow cytometry for the detection of low levels of aneuploid lymphoblastic leukemia cells ~n bone marrow *Cytometiy* 1997, 30, 47-53.
9. Latt, S. A.; Stetten, G. Spectral Studies on 33258-Hoechst and Related Bisbenzimidazole Dyes Useful for Fluorescent Detection of Deoxyribonucleic-Acid Synthesis *Journal of Histochemistry & Cyto Chemistry* 1976, 24, 24-33.
10. Krishan, A. Rapid DNA content analysis by the propidium iodide-hypotonic citrate method *Methods Cell Biol.* 1990, 33, 121-25.
11. Kapuscinski, J.; Skoczylas, B. Fluorescent Complexes of Dna with Dapi 4',6-Diamidine-2-Phenyl lndole.2Hcl Or Dci 4',6-Dicarboxyam ide-2-Phenyl lndole *Nucleic Acids Research* 1978, 5, 3775-99.
12. BORISOVA, O. F.; TUMERMAN, L. A. [LUMINESCENCE OF ACRIDINE ORANGE AND NUCLEIC ACID COMPLEXES. J 810 *fizika* 1964, 130, 537-44.
13. Jones, L. J.; Gray, M.; Yue, S. T.; Haugland, R. P.; Singer, V. L. Sensitive determination of cell number using the CyQUANT (R) cell proliferation assay *Journal of Immunological Methods* 2001, 254, 85-98.
14. Yun, K., Lee, J., Park, J., Kim, S., Lee, S., Kim, S. H., Lee, J. O., Lee, S. E., Park, J. G., and Yoon, G. S. Detecting nucleic acid hybridization comprises using nucleic acid intercatator, and detecting the quantity of light generated. Yun, K., Lee, J., Park, J., Kim, S., Lee, S., and LG ELECTRONICS INC. [US2003092055-A1; KR2003035247-A].
15. Lee, J. O., Yun, K. S., Park, J. K., Kim, S. H., Kim, T. H., Lee, S. E., Park, J. G., and Yoon, O. S. Detecting DNA, for analyzing samples quickly, comprises hybridizing a target with an immobilized DNA probe, fixing an intercalator, introducing electrochemiluminescent fluid, applying a voltage, and analyzing chemiluminescence. LG ELECTRONICS INC. [US20021 06682-Al; KR2002064805-A; KR386606-B].
16. Hurley, I. and Rabbani, E. Nucleic acid hybridization assay composition for hybridization assay procedures. ENZO DIAGNOSTICS INC. [U.S. Pat. No. 5,998,135-A; U.S. Pat. No. 6,239,271-B1].
17. Chen, W.; Turro, C.; Friedman, L. A.; Barton, J. K.; Turro, N. J. Resonance Raman investigation of Ru(phen)(2)(dppz)(2+) and related complexes in water and in the presence of DNA *Journal of Physical Chemistry B* 1997, 101, 6995-7000.
18. Dandliker, P. J.; Holmlin, R. E.; Barton, J. K. Oxidative thymine dimer repair in the DNA helix *Science* 1997, 275, 1465-68.
19. Erkkila, K. E.; Odom, D. T.; Barton, J. K. Recognition and reaction of metallointercalators with DNA *Chemical Reviews* 1999, 99, 2777-95.
20. Hill, M. G.; Jackson, N. M.; Barton, J. K.; Kelley, S. O. Electrochemistry at DNA-modified surfaces: Evidence for long-range electron transfer through an extended pi-stack *Abstracts of Papers of the American Chemical Society* 1997, 214, I 44-INOR.
21. Sitlani, A.; Long, E. C.; Pyle, A. M.; Barton, J. K. Dna Photocleavage by Phenanthrenequinone Diimine Complexes of Rhodium(iii)—Shape-Selective Recognition and Reaction *Journal of the American Chemical Society* 1992, 114, 2303-12.
22. Sittani, A.; Barton, J. K. Sequence-Specific Recognition of Dna by Phenanthrenequinone Diimine Complexes of Rhodium(Iii)—Importance of Steric and VanDer-Waals Interactions *Biochemistry* 1994, 33, 12100-08.
23. Kielkopf, C. L.; Erkkila, K. E.; Hudson, B. P.; Barton, J. K.; Rees, D. C. Structure of a photoactive rhodium complex intercalated into DNA *Nature Structural Biology* 2000, 7, 117-21.
24. Barton, J. K., Jackson, B. A., and Hudson, B. P. New rhodium intercalating compounds useful for diagnosing and/or treating disorder due to the presence of base mismatches in nucleic acid duplexes. CALIFORNIA INST OF TECHNOLOGY. [OS20030 18020-Al; U.S. Pat. No. 6,777,405-B2].
25. Dupureur, C. M.; Barton, J. K. Structural studies of Lambda- and Delta-[Ru(phen)(2)dppz](2+) bound to d(GTCGAC) (2) Characterization of enantioselectivö intercalation *Inorganic Chemistry* 1997, 36, 33-43.
26. Holmlin, R. E.; Dandliker, P. J.; Hall, D. B.; Barton, J. K. Charge transfer through the DNA base stack: Chemistry at a distance *Abstracts of Papers of the American Chemical Society* 1997, 213, 335-1NOR.
27. Barton, J. K., Hill, M. G., and Kelley, S. O. New composition comprising a nucleic acid duplex which contains one or more electron donor and electron acceptor groups, one of which is an intercalating intercalative, redox-active group for diagnosing genetic diseases. CALIFORNIA INST OF TECHNOLOGY. [US6221 586-B1].

28. Uchida, K.; Pyle, A. M.; Morii, T.; Barton, J. K. High resolution footprinting of EcoRl and distamycin with Rh(phi)2(bpy)3+, a new photofootprinting reagent *Nucleic Acids Res.* 1989, 17, 10259-79.

29. Sitlani, A.; Barton, J. K. Shape-Selective Recognition and Reaction by Phenanthrenequinone Diimine Complexes of Rhodium(lii) *Abstracts of Papers of the American Chemical Society* 1992, 204, 479-INOR.

30. Chow, C. S.; Hartmann, K. M.; Rawlings, S. L.; Huber, P. W.; Barton, J. K. Delineation of Structural Domains in Eukaryotic 5S Ribosomal-Rna with A Rhodium Probe *Biochemistry* 1992, 31, 3534-42.

31. Chow, C. S.; Behien, L. S.; Uhlenbeck, O. C.; Barton, J. K. Recognition of Tertiary Structure in Transfor-Rnas by Rh(Phen)2Phi3+, A New Reagent for Rna Structure-Function Mapping *Biochemistry* 1992, 31, 972-82.

32. Baranov, V. I.; Quinn, Z.; Bandura, O. R.; Tanner, S. D. A sensitive and quantitative element-tagged immunoassay with ICPMS detection *Analytical Chemistry* 2002, 74, 1629-36.

33. Baranov, V. I.; Quinn, Z. A.; Bandura, D. R.; Tanner, S. D. The potential for elemental analysis in biotechnology *Journal of Analytical Atomic Spectrometry* 2002, 17, 1148-52.

34. Zhang, C.; Zhang, Z. V.; Yu, B. B.; Shi, J. J.; Zhang, X. R. Application of the biological conjugate between antibody and colloid Au nanoparticles as analyte to inductively coupled plasma mass spectrometry *Analytical Chemistry* 2002, 74, 96-99.

35. Quinn, Z. A.; Baranov, V. I.; Tanner, S. D.; Wrana, J. L. Simultaneous determination of proteins using an element-tagged immunoassay coupled with ICP-MS detection *Journal of Analytical Atomic Spectrometry* 2002, 17, 892-96.

36. Li, F. M.; Armstrong, D. W.; Houk, R. S. Behavior of bacteria in the induct

37. Zhang, B.; Li, F. M.; Houk, R. S.; Armstrong, O. W. Pore exclusion chromatography-inductively coupled plasma-mass spectrometry for monitoring elements in bacteria: A study on microbial removal of uranium from aqueous solution *Analytical Chemistry* 2003, 75, 6901-05.

38. Binet, M. R. B.; Ma, R. L.; Mcleod, C. W.; Poole, R. K. Detection and characterization of zinc- and cadmium-binding proteins in *Escherichia coli* by gel electrophoresis and laser ablation-inductively coupled plasma-mass spectrometry *Analytical Biochemistry* 2003, 318, 30-38.

39. Zhang, V. S.; Zhang, Z. V.; Suzuki, K.; Maekawa, T. Uptake and mass balance of trace metals for methane producing bacteria *Biomass & Bioenergy* 2003, 25, 427-33.

40. Sharma, N. C.; Sahi, S. V.; Jam, J. C. Sesbania drummondii cell cultures: ICP-MS determination of the accumulation of Pb and Cu *Microchemical Journal* 2005, 81, 163-69.

41. Prange, A.; Profrock, D. Application of CE-ICP-MS and CE-ESI-MS in metalloproteomics: challenges, developments, and limitations *Analytical and Bioanalytica Chemistry* 2005, 383, 372-89.

42. Ranney, D. F. and Quattrone, A. J. Selective assay of cellular DNA in presence of cell debris—by measuring fluorescence enhancement of fluorochrome in presence of metal ion co-factor. UNIV TEXAS SYSTEM. [U.S. Pat. No. 4,423,153-AJ.

43. Muehlbauer, P. A. and Schuler, M. J. Detecting numerical chromosomal abnormalities, e.g. aneuploidy or polyploidy, by treating a mitotic cell with a mitotic marker and a quantitative DNA stain, and quantifying the amount of DNA in the cell using the quantitative DNA stain. PFIZER PROD INC, Muehlbauer, P. A., and Schuler, M. J. [WO2003046218-A; EP1316619-A; EP1316619-Al; US2003104461-Al; CA241 3177-Al; WO200304621 8-Al; J P2003210198-A; AU2002347468-Al; KR2004062979-A; N 02004021 80-A; CNI 606623-Al. ively coupled plasma: Atomization and production of atomic ions for mass spectrometry *Analytlcal Chemistry* 2005, 77, 1407-13.

44. Darzynkiewicz, Z., Li, X., and Traganos, F. Labelling DNA strands—using halogenated deoxy-nucleotide triphosphate, enzyme and labelled anti24 hatogenated deoxy-nucleotide antibody. NEW YORK MEDICAL, C. O. L. L., Traganos, F, Li, X, and Darzynkiewicz, Z [EP851939-A, WO9708345-A, WO9708345-Al; EP851939-A1; U.S. Pat. No. 5,912,126-AJ.

45. Darzynkiewicz, Z. D., Li, X., Traganos, F. N., and Melarned, M. R. Detection of halogenated precursors incorporated into DNA—useful for prognosis of tumours and evaluation of potential genotoxins NEW YORK MEDICAL, C O L L [WO9533070-A; EP711356-A; WO9533070-A1; AU9526047-A; EP7I 1356-Al; U.S. Pat. No. 5,747,258-A].

46. Morrison, O. R. Measuring metastatic activity of tumours—comprises quantitative detection of urokinase and DNA to evaluate the presence of tumour cells with invasive character. NASA US NAT AERO & SPACE ADMIN. [US5869238-A].

47. Bacus, J. W. and Cud, P. S. Kit for quantitation of cell nuclei components contg. microscope slides having a reference area and a specimen area and containers of stain. CELL ANALYSIS SYSTEMS INC and BECTON DICKINSON, C. O. [EP314293-A2; EP314293-A; JP1127956-A; US5109429-A; US5272759-A; EP314293-B1; DE3853254-G; US5485527-A].

48. Dolbeare, F. A. and Gray, J. W. Flow cytometric or spectrophotometric measurement of total DNA—and incorporated halodeoxyuridine. REGLISSE ZAN, S. A. R. L. [U.S. Pat. No. 4,780,406-A].

49 Dertinger, S, Torous, D, and Tometsko, K Method for enumeration of micro-nuclei events in erythrocyte populations—uses single laser flow cytometry on alcohol fixed blood from bone marrow or peripheral blood. LITRON, L. A. B. [US5858667-A].

50. Kamentsky, L. D. Cytometric measurement of DNA content of cells to determine cell mitosis—by creating histogram of cell counts versus integrated fluorescent light corrected to remove statistical errors, focusing problems and background COMPUCYTE CORP [EP793830-A, WO961 1448-A, WO961 1448-Al, AU9538889-A; US5633945-A; EP793830-A1; J P1 0508690-W; IL1 15506-A].

51. Orfao de Matos Correia e Vale and Orfao de Matos, C. O. R. R. Cell cycle analysis in heterogeneous sample—using pool of monoclonal antibodies labelled with same fluorochrome. UNIV SALAMANCA. [EP798386-A; EP798386-Al; ES2112211-A1; ES2112211-B1; EP798386-B1; DE69728925-EJ.

52. Oda, V., Ishihama, V., and Tabata, T. Assaying one or more biomolecules in sample, involves adding internal standard substance (metabolically isotope-labeled biomolecule) or cell having internal standard substance, to sample, and measuring sample by mass spectrometer. EISAI CO LTD and MITSUI KNOWLEDGE IND CO LTD. EWO20050501 88-Al].

53. Maeda, M., Akimoto, K., Hori, J., Murayama, R., Tabata, J., and Bando, K. Detecting target gene with specific sequence by adding intercalator to double-stranded nucleic acid formed by adding sample having single-stranded target, to probe, performing photo irradiation and detecting intercalator bound nucleic acid. MATSUSHITA ELECTRIC IND CO LTD and MICROTEC CO LTD. (WO2005103695-A1].
54. Barton, J. K. and Junicke, H. New metallo-intercalators useful for e.g. diagnosing genetic disorders. CALIFORNIA INST OF TECHNOLOGY, Barton, J. K., and Junicke, H. [WO200257492-A; WO200257492-A1; US2002155470-A1; EP1349962-A1; AU20022451 16-A1; JP2004522739-W; US6808884-B2; US20051 48772-A1].

What is claimed is:

1. A method to quantify the number of cells in a sample comprising cells, the method comprising:
   (a) culturing the sample with an element to passively accumulate the element in the cells in the sample;
   (b) washing the cells to remove non-accumulated element;
   (c) measuring the element in a known quantity of the cells by elemental analysis to determine the amount of accumulated element per cell;
   (d) measuring the element in the sample by elemental analysis; and
   (e) quantifying the number of cells in the sample by dividing (d) by (c).

2. A method to quantify antigen content per cell in a cell sample wherein the cells of the sample comprise an antigen, comprising:
   (a) culturing the cells of the sample in the presence of a first element wherein the cells passively accumulate the first element;
   (b) calculating the number of cells in the sample;
   (c) removing non-accumulated first element;
   (d) incubating the cells with antigen specific affinity products labeled with a second element;
   (e) removing unbound affinity products;
   (f) simultaneously measuring the passively accumulated first element and the bound affinity product labeled with a second element tag by elemental analysis; and
   (g) calculating the antigen content per cell.

3. The method of claim 2 where in step (a) the concentration of the first element is between 1 ppt and 10 ppm.

4. The method of claim 2 where in step (b) the number of cells is calculated using a hemocytometer or a Coulter counter.

5. The method of claim 2 where in step (d) the antigen specific affinity product is an antibody complex comprising a secondary antibody labeled with an element tag that binds to a primary antibody, and wherein the primary antibody is specific to the antigen.

6. The method of claim 2 where in step (d) the cells are incubated with at least two classes of antibodies, each class of antibodies specific to different classes of antigens and each class of antibody is labeled with unique element tag.

7. The method of claim 2 further comprising a step after step (e) wherein the cells are dissolved to generate a relatively homogeneous sample before determining the amount of first element and second element by performing solution elemental analysis.

8. The method of claim 7 wherein the cells are dissolved in an acid solution.

9. The method of claim 2 where for step (b) and (f) a mass spectrometer-based flow cytometer is used.

* * * * *